United States Patent
Higo et al.

[11] Patent Number: 6,006,130
[45] Date of Patent: Dec. 21, 1999

[54] IONTOPHORESIS ELECTRODE AND IONTOPHORESIS DEVICE USING THE ELECTRODE

[75] Inventors: Naruhito Higo; Kenji Mori; Kazuya Katagai; Katsuhiro Nakamura, all of Ibaragi-ken, Japan

[73] Assignee: Hisamitsu Pharmaceutical Co., Saga-ken, Japan

[21] Appl. No.: 08/750,712

[22] PCT Filed: Jun. 15, 1995

[86] PCT No.: PCT/JP95/01193

§ 371 Date: Feb. 24, 1997

§ 102(e) Date: Feb. 24, 1997

[87] PCT Pub. No.: WO95/35132

PCT Pub. Date: Dec. 28, 1995

[30] Foreign Application Priority Data

Jun. 17, 1994 [JP] Japan .................................. 6-159406
Jun. 17, 1994 [JP] Japan .................................. 6-159410
Aug. 18, 1994 [JP] Japan .................................. 6-218162
Sep. 17, 1994 [JP] Japan .................................. 6-248699

[51] Int. Cl.$^6$ ........................................ A61N 1/30
[52] U.S. Cl. .................... 604/20; 607/134; 607/149; 604/501
[58] Field of Search .............. 604/20–21, 501; 607/134, 149

[56] References Cited

U.S. PATENT DOCUMENTS 569,380  10/1896  Hollingsworth .
4,301,794  11/1981  Tapper .
4,927,408  5/1990  Haak et al. .
5,158,537  10/1992  Haak et al. .

FOREIGN PATENT DOCUMENTS 60-188176  9/1985  Japan .
63-200774  8/1988  Japan .
1-280476  11/1989  Japan .
474030  6/1991  Japan .
3-268769  11/1991  Japan .
4-208166  7/1992  Japan .
4-224770  8/1992  Japan .
4-312471  11/1992  Japan .

*Primary Examiner*—Mark Bockelman
*Attorney, Agent, or Firm*—Lane, Aitken & McCann

[57] ABSTRACT

This invention relates to an iontophoresis electrode which is applicable to mucous membranes and oral mucous membranes, and especially capable of sticking directly on human oral mucous membranes and excellent in efficiently administering medicine and extremely easy to handle and lightweight.

An iontophoresis electrode (Ka) of this invention comprises a backing layer (1) and, a conductive layer for current dispersion (2) made of silver or silver chloride that laminated on the backing layer (1) and, a spacer layer (3) of film, sheet, or cloth shape which is made of dried polymer layer with water soluble and swelling properties and laminated on the conductive layer for current dispersion, and can be sticked to the oral mucous membrane.

2 Claims, 10 Drawing Sheets

IONTOPHORESIS ELECTRODE AND IONTOPHORESIS DEVICE USING THE ELECTRODE

TECHNICAL FIELD

This invention relates to an iontophoresis electrode and a device using this iontophoresis electrode. More specifically, this invention relates to an iontophoresis electrode and a device using this iontophoresis electrode which are applicable to mucous membranes and oral mucous membranes, and especially capable of sticking directly on human oral mucous membranes and excellent in efficiently administering medicine and extremely easy to handle and lightweight.

BACKGROUND ART

Generally when medicinal substances such as physiologically active agents are administered into the body through oral administration applied as a general method for applying medicine, administering the medicinal substances is impossible because the medicinal substances are likely to undergo metabolic changes in the liver after being absorbed and the absorbability of the medicine is generally poor. Therefore in spite of the fact that many medicines promise excellent medical effects, a convenient method utilizing medicines was not yet established and the method of administering medicines must be relied on an injection which is troublesome at a clinical site and gives pain to the patients. In these circumstances, a simple administrative technique which is also capable of avoiding the effects of initial passage of the medicine through the liver is desired. Methods which avoid effects of initial passage through the liver include administration through the skin, nose, rectum, lungs and oral mucous membranes. However each of these paths has physical limits for most medicines as to the amount of the medicine being absorbed to obtain a sufficient clinical effect. This served to demonstrate the need for methods for facilitating absorption.

In a search to resolve these problems, most attention in recent years has focused on iontophoresis as a method to effectively administer ionic medicinal substances into the body by absorption through the skin. Iontophoresis is a device which causes absorption of the medical substances to occur by means of an electrical current passed through the ionized medicinal substances. In the iontophoresis device, anode and cathode iontophoresis electrodes are sticked to the skin at regular intervals and an electrical current generated by a current generator is led through the wire leads between the iontophoresis electrodes. Many such iontophoresis devices have previously been employed (Japanese Patent Laid-Open No. 60-188176 and Japanese Patent Publication No. 4-74030). In these patents, the iontophoresis device is provided with a anode iontophoresis electrode containing the positively ionized medicinal substances or is provided with a cathode iontophoresis electrode containing the negatively ionized medicinal substances. A conductive layer filled with sodium chloride and the like is generally utilized for iontophoresis electrodes not containing a medicinal substances.

PROBLEMS TO BE SOLVED BY THE INVENTION

However the above mentioned iontophoresis electrodes and the device utilizing them had the following problems.

a. A high possibility of burns of oral mucous membranes through an electrical energization exists when attempting medical treatment by absorption of the medicinal substances through the oral mucous membranes. Further, since the oral cavity is normally moist with saliva the possibility of burns is high not only at the contact site between the iontophoresis electrodes and oral mucous membrane, but over a wide range. This method was thus not only lacking in safety but has the drawback of causing pain to the patient by applying an electrical stimulation that is too strong.

b. Leakage and deterioration of the medicinal substances occur in its flowing process and the potency of the medicinal substances is unstable with the elapse of time due to the need to dissolve the medicinal substances in it so it can be adequately absorbed in the oral mucous membranes. When medicinal substances are peptide compounds of polymer physiologically active agents, they cause a serious problem to stability with the elapse of time.

c. A problem also occurs due to ions emitted from the iontophoresis electrode through electrical current flow and ions contained in the spacer layer and medicine layer, acting to block the flow (or electrophoresis) of the medicinal substances.

d. Continuous parallel current generating devices and intermittent parallel current generating devices have been proposed for use when trying to administer medicine by absorption through the skin by means of an iontophoresis device to attain a treatment effect. These devices, however, have the drawback that skin irritation causes as the resistance of the skin gets larger.

e. A method has been proposed for administering medicine into the body through the skin more effectively by using a pulse depolarizing current generator generating a pulse of high frequency current for eliminating the frequency-dependent high polarizing impedance component from the skin tissue to lower the level of irritation. However when administering medicine through the skin the resistance tends to still be too high even when this method is utilized. Moreover, the medicine may not be absorbed due to complex skin tissue structures with the added drawback that medicine composed, in particular, of polymer peptide compounds is not absorbed in sufficient amounts and the medicine has an inadequate effect.

f. A problem during actual use is that a large-size current generator must be prepared to obtain adequate absorption with the iontophoresis device. The mucous membrane in the human body is an extremely minute area and is covered with mucous constituents containing water so that iontophoresis electrodes proposed up until now require moisture gel layers or unnecessary and unrealizable adhesive constituents and the device has to be large to include electrodes to supply water during use. Additional drawbacks are a complicated structure making the device difficult to operate during use and also difficult to stick electrodes to local areas. The actual state of the art is such that a practical mucous membrane iontophoresis electrode and iontophoresis device for mucous membrane have not been developed.

OBJECT OF THE INVENTION

In view of the above problems, it is an object of the present invention to provide an iontophoresis electrode and a device using it which are both small and lightweight for securing onto the mucous membrane and absorbing the electrolytic mucous constituents including water from the mucous membrane during use and further having an adhesive layer containing medicinal substances with electrically conductive properties and utilizing the electrolytic constituents in the mucous, in particular, by means of external electrical circuit sticked to the mucous membrane.

Another object of the present invention is to provide an iontophoresis electrode excellent for bringing about high absorbability of peptide compounds administered into the body through the mucous membranes or oral mucous membranes and further for extremely low stimulation (irritation) of the mucous membranes and oral mucous membranes during administration of the medicinal substances.

A further object of the present invention is to provide an iontophoresis electrode excellent for bringing about high absorbability of the medicinal substances administered into the body through the mucous membranes or oral mucous membranes without interfering with flow of the medicinal substances while power is applied, and further for extremely low stimulation (irritation) of the mucous membranes and oral mucous membranes and excellent in discharging and stable preservation of the medicine during administration into the body.

A still further object of the present invention is to provide an iontophoresis device for the oral mucous membrane excellent for bringing about high absorbability of medicinal substances containing polymer physiologically active agents administered through the oral mucous membranes, and further for extremely low electrical stimulation (irritation) of the oral mucous membranes during administration of the medicinal substance.

DISCLOSURE OF THE INVENTION

In order to accomplish the objects of the invention, the iontophoresis electrode and device using the electrode are comprised as stated below.

The iontophoresis electrode according to claim 1 comprises a backing layer, and a conductive layer for current dispersion laminated on the backing layer and, a spacer layer laminated on the conductive layer for current dispersion.

The iontophoresis electrode according to claim 2 is based on claim 1 and has the spacer layer formed wider than the conductive layer for current dispersion.

The iontophoresis electrode according to claim 3 is based on claim 1 or 2 and has the conductive layer for current dispersion made of silver or silver chloride.

The iontophoresis electrode according to claim 4 is based on any one of claims 1 through 3 and has the spacer layer made of a dried polymer layer with water soluble and swelling properties with film, sheet, or cloth shape with sticking property to an oral mucous membrane.

The iontophoresis electrode according to claim 5 is based on any one of claims 1 through 3 and has the spacer layer comprising an ionic polymer layer, a medicinal substance layer and a water absorbing layer.

The iontophoresis electrode according to claim 6 is based on any one of claims 1 through 5 and medicinal substances are contained in or sticked to the spacer layer or the medicinal substance layer.

The iontophoresis electrode according to claim 7 is based on any one of claims 1 through 5 and medicinal substances are contained in and/or sticked to the surface of the spacer or the dried polymer layer with water soluble and swelling properties or the medicinal layer in dried state.

The iontophoresis electrode according to claim 8 is based on either of claims 6 or 7 has the medicinal substances comprising a physiologically active substance having a molecular weight of $1 \times 10^2$ through $3 \times 10^6$.

The iontophoresis electrode according to claim 9 is based on any one of claims 1 through 8 and is used as a preparation for iontophoresis through the mucous membrane or oral mucous membrane.

The iontophoresis device according to claim 10 has the iontophoresis electrode according to any one of claims 1 through 4 (hereafter reference device), the iontophoresis electrode according to any one of claims 5 through 8 (hereafter donor device), an electrical circuit to connect the each conductive layer for current dispersion of the reference device and the donor device, and a power supply connected to the electrical circuit.

The iontophoresis device according to claim 11 is based on claim 10 has a depolarization system to depolarize the reference device and the donor device connected to the power supply.

The iontophoresis device according to claim 12 is based on claim 11 and the depolarization system has a pulse generator connected between the donor device and the power supply, and a switch connected between the donor device and the power supply.

The iontophoresis device of one according to claim 13 is based on claims 10 through 12 and the conductive layer for current dispersion is formed into two or more segments in approximately a concentric, or semicircular, or rectangular shape, and each of the spacer layer is laminated on each surface of the segmented conductive layer for current dispersion.

The iontophoresis device according to claim 14 has the backing layer, the conductive layer for current dispersion formed into two or more segments, in approximately a concentric, or semicircular or rectangular shape, and the spacer layer each of which is laminated on each surface of the segmented conductive layer for current dispersion.

The iontophoresis device according to claim 15 is based on claim 14 and the segmented spacer layers are formed with the dried polymer layer with water soluble and swelling properties, and medicinal substances are contained or sticked to at least one of the layers.

The iontophoresis device according to claim 16 is based on any one of claims 13 through 15 has a power supply comprised of a light-weight battery etc. between the backing layer and the segmented conductive layer for current dispersion.

The iontophoresis device according to claim 17 is based on any one of claims 13 through 15 has an electrical circuit to electrically connect each of the segmented conductive layer for current dispersion and, the power supply connected to the electrical circuit.

The iontophoresis device according to claim 18 is based on claim 17 having the depolarization system to depolarize the reference device and said donor device connected to the power supply.

The iontophoresis device according to claim 19 is based on claim 18 has the depolarization system provided with a pulse generator connected between the donor device and the power supply and, a switch connected between the conductive element and the power supply.

The iontophoresis device according to claim 20 is based on any one of claims 10 through 19 and is applied through the mucous membranes or the oral mucous membranes.

Here, material having at least non-permeable properties for the medicinal substances is utilized as the backing layer. This property prevents leakage of the medicinal substances or the additive added as required. Examples of materials utilized as the backing layer include film, sheet, or felt made from synthetic resin; woven fabric, or non-woven fabric made from natural or synthetic fibers; paper, synthetic paper or composite thereof or one or more of these materials laminated with synthetic resin film. As a specific example, a film or sheet of synthetic resin can be used alone or as multiple laminations of layers of polyethylene, polypropylene, polyethylene terephthalate, polystyrene, ABS, polyvinyl chloride, polyvinylidene chloride, plasticized vinyl acetate copolymer, plasticized vinyl acetate-vinyl chloride copolymer, polyamide, polyurethane, cellophane, cellulose acetate or ethyl cellulose, etc. Further, these synthetic resin films or sheets laminated with synthetic paper, or metal leaf such as aluminum leaf or tin leaf, or coated with aluminum vapor deposition or ceramic or lamination of these materials can also be used.

On the surface of the backing layer, as needed, a recess to accommodate and keep the medicinal substances and the conductive layer for current dispersion is formed. There are no particular restrictions on the shape of the recess or contour of the support layer, however, generally a circular, elliptical, or rectangular shape is preferable.

The electrode material used in the conductive layer for current dispersion includes silver, silver chloride, platinum, platinum black, carbon, aluminum, steel, lead, gold, copper, molybdenum, titanium, nickel, stainless steel, palladium, iridium or a conductive rubber in which the above-mentioned metals are dispersed in natural rubber or synthetic resin, and cross-linked as needed, or a conductive resin which silver, copper, carbon powders or carbon fiber is dispersed in epoxy resin, or pvc resin. Of these materials, silver or silver chloride is preferred.

For laminating the conductive layer for current dispersion on the backing layer, several methods such as a method for applying and drying electrode material mixed with printing ink for the electrical circuit wiring on the layer, a method for rolling, extending and hardening the material on the layer, a method for vapor-deposition of the material on the layer, and a method for photo-etching of the material, are known and employed.

When the conductive layer for current dispersion are segmented into two or more pieces, the material for the conductive layer is laminated on the backing layer in adjusting to each contour. Further, it is also preferable that a protective layer made of electrical conductive material is partially or entirely laminated between the electrical conductive layer and a spacer layer so as to avoid influences such as deterioration caused by medicines according to the type of the electrical conductive layer for dispersing electrical current. In addition, it is possible to make a small ionphotoresis device by arranging light weight cells such as a button-shaped cell or a sheet-like cell or the like between the backing layer and the electrical conductive layer for current dispersion.

As materials forming the spacer layer, natural organic polymer film or sheet, or woven fabric or non-woven fabric of natural fiber or synthetic fiber, felt, film or sheet of synthetic resin capable of adhering or dispersing or impregnating medicines such as physiologically active substances or the like. For these materials, water-soluble polymer material, hydrophobic polymer material and hydrophilic polymer material and natural materials or composites made from these materials are known and used. Other possible materials include synthetic paper and natural paper. When the medicinal substances are administered to moucous membrane, particularly oral mucous membrane, dried polymer material with water soluble and swelling properties is preferred. Specific examples of dried polymer material with water soluble and swelling properties are preferably in the form of a film, sheet, or woven fabric made of polyvinyl alcohol, gelatin, agar, starch, xanthan gum, gum of arabic, tragacanth gum, karaya gum, echo gum, locust bean gum, sodium alginate, pectin, methyl cellulose, ethyl cellulose, propyl cellulose, ethylmethyl cellulose, hydroxyethyl cellulose, hydroxypropyl cellulose, carboxy methyl cellulose, cellulose acetate phthalate, polymethylvinyl ether, polyvinyl pyrrolidone, carboxyvinyl polymer, caseine, albumin, chitin, chitosan, polyacrylic acid, poly(sodium acrylate) and its crosslinked product, and as needed one or more softening agents chosen from glycerine, propylene glycol, polyethylene glycol, 1,3-butanediol and sorbitol.

The above constituents are dissolved into the spacer layer on the donor device side along with the medicinal substances to cause the layer to be conductive, but a support electrolytic material can be added in appropriate amounts as required in the same manner as the so-called gel for electrophoresis is used The spacer layer on the reference device side can be added with electrolytes such as sodium chloride, sodium carbonate, potassium citrate in amounts normally of about 0.001 to 15% to provide ample conductivity.

Dried polymer layer with water soluble and swelling properties obtained in this way is a soft film or sheet or cloth-like product which can be closely contacted with and joined to a skin, so that it has some practical advantages that skin contact resistance is extremely low and this is effective not only for the medicinal substance penetration into the mucous membrane, but also the overall structure can be adhered to and supported at the skin without any other application of adhesive tape to the skin. Using natural resin polysaccharides such as karaya gum as the base material of the polymer layer provides not only a gel with good electrochemical superior conductive gel but also a preferable skin adaptation, in particular, a mucous membrane adaptability due to a pH buffering with natural polymer acidic structure or a skin protection, a remarkable high water retension and a suitable skin adhesion or the like.

By formulation of these spacer layers, it is common that nearly same electrochemical care must be taken as that of the so-called gel for electrophoresis and mainly the type and amount of medicinal substances to be administered, the sticking time in use, the battery output and skin contact surface area must be considered to ensure the necessary ion mobility and conductivity are attained.

Also, a spacer layer can be formed not only by only one layer but by a multi-layer as a laminate of an ionic polymer layer, a medicinal substance layer, and a water absorbing layer. Integrated laminations of these layers are made by utilizing methods such as laminate compression or through binder.

The spacer layer can be formed to about 1.01 to 1.3 times the width of the conductive layer for current dispersion in order to lower stimulation (irritation) of the oral mucous membranes and ensure good absorption of the medicinal constituents in a short time. In particular, when the spacer layer is a laminate or multi-layer, the layer containing the medicinal agent should preferably be formed wider than the conductive layer for current dispersion in order to ensure the medical constituents absorbed through the mucous membranes into the body over a wide area.

A positive ion exchange polymer layer having only a positive ion exchange group, a negative ion exchange polymer layer having only a negative ion exchange group, a dual ion exchange polymer layer having both ion exchange groups distributed uniformly into the membrane, a zwiter ion exchange polymer layer with both ion exchange groups distributed into the layer and mosaic-charge ion exchange polymer layers existing in parallel in polymer regions having microstructures with ion exchange radicals for each of positive ions and negative ions are listed as examples of ionic polymer layers. These are selected for use as needed according to the ionization characteristics of the medicinal substances.

Polar groups having positive and negative charges in the above mentioned type of ionic polymer layers include sulfonic acid, phosphonic acid, sulfuric ester, phosphoric ester, carboxylic acid, phenol type hydroxyl group, primary to quaternary ammonium base, sulfonium base, onium base, pyridinium base etc.

There are no particular restrictions on the manufacturing method for the ionic polymer layer, although there are a method of dispersing fine powder particles of the existing ion exchange resin in a colloidal state for forming a membrane shape with binding agents of polyethylene, polystyrene, phenol resin, methyl-methacrylate and synthetic rubber etc. for instance; another method of introducing an exchange group after polymerizing such vinyl monomers as styrene, vinylpyridine, vinyl sulfonic butyl ester and also crosslinking monomers such as divinyl benzene with film of polyolefin, polyvinyl chloride, fluororesin; another method for vaporizing the solvent after dissolving an inert, linear polymer such as copolymer of acrylonitrile and vinyl chloride into a polymer electrolyte solution of poly-(styrene sulfonic acid), polyvinylimidazole quarternary salt; yet another method for taking a mixture of vinyl monomers such as styrene and crosslinked monomers such as divinyl benzene, adding this with fine powder of thermoplastic polymers and plasticizer to obtain a paste mixture, coating this on the support body of cloth or net to form a membrane shape and heating the thermo plastic polymers to produce a gel and at the same time produce a polymer film by polymerizing the monomer and finally subjecting this to an ion exchange group; and still another method in the case of styrene, divinyl benzene and negative ion exchange group adding a basic monomer, polymerize the sheet-shaped product and subjecting it to an ion exchange group.

Various methods can be utilized for laminating the ionic polymer layer onto the conductive layer for current dispersion such as a method for joining by the water absorbing layer or laminate integration during application of conductive material for the current dispersion.

As medicinal substance layers, a single layer of medicinal substance fixed by application to an ionic polymer layer or to an water absorbing layer is sometimes used. Another method is a composite layer of medicine contained in liquid form in a so-called medicine support layer and later dried, is formed from materials listed for the water absorbing layer. The medicinal substances are preferably contained in or adhered to the medicinal substance layer in a dried state. This procedure improves the stability of the medicine with the elapse of time and also prevents leakage or deterioration of the medicinal substances.

Placing the medicinal substance layer on the outer spacer layer, the spacer layer allows effective absorption of the medicinal substances into the body and also prevents disintegration of the medicinal substances within the conductive layer for current dispersion.

The sequence of lamination of the water absorbing layer, ionic polymer layer, and medicinal substance layer on the conductive layer for current dispersion can be changeable depending on the types of the medicinal substances and the method of medical treatment. For instance, when the water absorbing layer is first laminated on the conductive layer for current dispersion followed by the ionic polymer layer and medicinal substance layer, the medicinal substances are absorbed quickly. On the other hand, when the ionic polymer layer is first laminated on the conductive layer for current dispersion, the medicinal substances are controlled to be absorbed slowly.

Materials preferably used for the water absorbing layer under nonaqueous conditions normally include but are not limited to the following, and they may be used solely or in combination: nonwoven fabric, woven fabric, paper, gauze, absorbent cotton, open-cell foam of polyolefine such as polyethylene and polypropylene, porous film of polyamide foam or polyurethane foam; natural polysaccharides such as karaya gum, tragacanth gum, xantham gum, starch, gum arabic, echo gum, locust beam gum, and joran gum; gelatin, pectin, agar, sodium alginate or polyvinyl alcohol or its saponified product, polyvinyl formal, polyvinyl methyl ether and its copolymer, polyvinyl pyrrolidone and its copolymer, poly(sodiuum acrylate), sodium carboxymethyl cellulose, methyl cellulose, ethyl cellulose, propyl cellulose, ethylmethyl cellulose, hydroxymethyl cellulose, hydroxyethyl cellulose, hydroxypropylmethyl cellulose, hydroxypropyl cellulose, aqueous or soluble cellulose derivatives such as cellulose acetate phthalate, carboxylvinyl polymer, polyacryl amide and its derivatives, casein, albumin, chitin, chitosan, polyhemas, and its derivatives and their crosslinked products and their mixture with known plasticizers or softening agents as required such as ethylene glycol and glycerine, and soluble polymer and its hydrogel.

To increase conductivity, electrolytes such as sodium chloride, sodium carbonate, and potassium citrate may be added to the water absorbing layer.

Various methods are used to laminate the water absorbing layer on the ionic polymer layer and conductive layer for current dispersion, such as a method in which the material for the water absorbing layer is applied to the ionic polymer layer and conductive layer for current dispersion, and a method in which water-containing or dried water absorbing layer is laminated by press contact to the ionic polymer layer and conductive layer for current dispersion and, if necessary, dried.

To dissolve the medicinal substances contained in and/or adhering to the outermost surface of the ionic polymer layer or medicinal substance layer in dried state, water may be supplied to the ionic polymer layer and the water absorbing layer or the medicinal substance layer at the time of administration. For that purpose, a water supply layer may be provided adjacent to the ionic polymer layer or the water absorbing layer or the medicinal substance layer. As the water supply layer, water absorbing materials, which are sponge or porous materials, for impregnating medicine solution are used; specifically, they include paper materials as water absorbing paper etc., cloth materials as gause etc., fiber materials as absorbent cotton etc., synthetic resin open-cell foam bodies, and water absorbing resins.

Major requirements for the medicinal substances are; being electrically charged, being modifiable to carry an electric charge, or being able to form complexs with another compounds by hydrophobic interaction and resultant complexs being able to hold electric charge. However, in some cases an electric charge is unnecessary. Factors for selecting appropriate medicinal substances include those based on the conductivity of individual medicinal substances, for instance the mobility of the medicinal substances in the solution when electric current is flowed. To provide sufficient conductivity, electrolytes such as sodium chloride, sodium carbonate, and potassium citrate may be added.

The amounts of the medicinal substances administered to a patient are determined for each substance so as to keep a predetermined effective medicine concentration in the blood for necessary period of time. Thereby the Size of the backing layer, the area and thickness of the medicinal substance release surface (or medicinal substance layer) of the iotophoresis electrode for buccal mucosal administration, iontophoresis potential and time for administration are determined.

Methods for forming the medicinal substance layer on the spacer layer, ionic polymer layer, and water absorbing layer include a method in which the medicinal substances are directly applied to the spacer layer, ionic polymer layer, and water absorbing layer, and another method in which the application is made to the ionic polymer layer through the water absorbing layer.

The preparation form may be any of water solution, suspension, ointment, gel, and cream. However, a dried state is preferable for improving storage stability of polymer medicinal substance such as physiologically active agents.

Two or more kinds of medicinal substances may be used simultaneously as required. These medicinal substances may be contained in or adhered to the spacer layer and to the medicinal substance layer as required in the forms of compounds derived as ester, compounds derived as amide, compounds derived as acetal, or medically acceptable inorganic and organic salts.

Methods for adhereing the dried medicinal substances to the outermost surface of the spacer layer and medicinal substance layer include spray drying and freeze drying (lyophilization) together with a binder as required.

The amounts of the medicinal substances contained in the space layer and the medicinal substance layer, and administered to a patient are determined for each substance so as to keep a predetermined effective medicine concentration in the blood for necessary period of time. Thereby the size of the backing layer, the area and thickness of the medicinal substance release surface are determined.

The medicinal substances may be any of remedial substances and their combinations in major remedial fields as long as they can be dissolved and diffused in water and saliva and include but are not limited to the following; anesthetics, anodynes, anti-anorexic medicines, vermicides, anti-asthmatic medicines, anti-convulsion medicines, anti-diarrhea medicines, anti-tumor medicines, anti-Parkinson's disease medicines, anti-urtication medicines, sympathetic nerve agonists, xanthines, cardiovascular medicines such as potassium passage antagonist, antifebriles, beta (b)— antagonists, anti-arrhythmic medicines, hypotensives, diuretics; vasodilators including those for the entire body, coronary vessels, peripheral capillaries; anti-migraine medicines, anti-intoxification medicines, anti-emesis medicines, central nervous system stimulants, cough and cold medicines, decongestants, diagnostic agents, hormones, parasympathetic nerve inhibitors, mind stimulants, sedatives, tranquilizers, anti-inflammation medicines, anti-depressants, anti-mental disease medicines, anti-vertigo medicines, anti-anxiety medicines, anesthetic antagonists, anti-cancer medicines, soporifics, anti-immune medicines, muscle relaxants, anti-viral medicines, antibiotics, anorexice agents, emesis sedatives, anti-choline agents, antihistamines, contraceptives, anti-thrombosis medicines, anti-mycosis medicines, and anti-inflammation medicines. Examples of the medicinal substances include but are not limited to; steroids such as estradiole, progesterone, norgestrel, levonorgestrel, norethindrone, medroxyprogesterone acetate, testosterone, and their ester; derivatives of nitro-compounds such as nitroglycerin and isosorbide dinitrate, nicotin, chlorphenylamine, terfenadine, triprolidine, hydrocortisone, oxicam derivatives such as piroxicam, ketoprofen, mucopolysaccharase such as thiomucarse, buprenorphine, fentanyl, naloxone, codeine, lidocaine, dihydroergotamine, pisotyline, salbutamol, terbutaline, prostaglandin such as misoprostol, enprostil, omeprazole and imipramine, benzamide such as metoclopramine, scopolamine; peptides such as growth releasing factor and somastatin, clonidine, dihydropyridine such as nifedepin, verapamil, ephedrine, pindolol, metoprolol, spironolactone, nicardipine hydrochloride, calcitriol; thiazide such as hydrochlorothiazide, flunarizine, sydnone imine such as molsidomin, sulfated polysaccharide such as heparin fraction and protein, and peptide such as insulin and its homology; calcitoning and its homology such as elcatomin, protamine, glucagon, globulin, angiotensin I, angiotensin II, angiotensin III, riblessin, vasopressin, somatostatin and its homology, growth hormon and oxytocin; anti-fungus medicines such as lanoconazole, itraconazole, fluconazole, miconazole, bifonazole and butenafine, and if necessary, salts of acids and bases pharmaceutically compatible with their compounds. Effective medicinal substances are preferably anesthetics, hormones, protein, pain-killers, or other low molecular cations. More preferable ones include but are not limited to; peptide or insulin of the peptide family, calcitonin, calcitonin-related gene peptide, vasopressin, desmopressin, protirelin (TRH), growth hormone, adrenal cortex exciting hormone (ACTH), corpus luteum forming hormone releasing hormone (LH-RH), growth hormone releasing hormone (GRH), nerve growth factors (NGF) and other release factors, angiotensin, parathyroid gland hormone, corpus luteum forming hormone (LH), prolactin, sex gland exciting hormone, pituitary gland hormone (e.g. HGH, HMG, HCG), growth hormone, somatostatin, somatomedin, glucagon, oxytocin, gastrin, secretin, endorphin, enkephalin, endocering, cholecystokinin, neurotensin, interferon, interleukin, transferein, erythropoietin, superoxide dismutase (SOD), filgrastim (G-CSF), vasoactive intestinal polypeptide (VIP), muramyl dipeptide, cortiocotropine, urogastrone, atrium-acting sodium diuretic peptide (h-ANP), histaglobulin, macrocortin, physiologically active proteins such as blood coagulating eighth factor and its chemical modification compound, and vaccines include but are not limited to such as whooping cough vaccine, diphtheria vaccine, tetanus vaccine, influenza vaccine, or lymphocytostic factors, fiber red blood cluster agents are listed. Among these, in particular peptide hormones are preferable.

Peptide compounds having physiologically active substances such as oligopeptides, polypeptides and macropeptides with a molecular count of 100 to 300,000 are used.

The following are listed as preferred specific examples of peptide compounds with physiologically active elements; for instance calcitonin, insulin, angiotensin, vasopressin, desmopressin, ferripressin, protirelin, progestational hormone discharge hormone, corticotropin, prolactin, somatotropin, thyrotropin, progestational hormone, kallikrein, parathyrin, glucagon, oxycitosin, gastrin, secretin, serum sex gland stimulation hormone, growth hormone, erythropoetin, angiotenshin, urogastrin, renin peptide hormones and their supplemental compounds; physiologically active proteins such as interferon, interleukin, transferin histaglobin, macrocorocin, blood coagulating eighth factor; and vaccines such as whooping cough vaccine, diphtheria vaccine, tetanus vaccine, influenza vaccine, or lymphocytostic factors, fiber red blood cluster agents are listed. Among these, in particular peptide hormones are preferable.

As additives when required, to the medicinal substances; solvents such as water, ethanol etc.; emulsifiers such as phosphatide acid derivatives, lecithin, cephalin, polyalkylene grycol etc.; absorbing promoters such as methyl laurate, methyl caprate, azone, oleic acid, pirothiodecane, 1-menthol, limonene, oil of peppermint etc.; dissolution agents or dissolution promotors such as crotamiton, ethylene glycol, diethylene glycol, triethylene glycol, propylene glycol, polyethylene glycol, polypropylene glycol, dimethyl sulfoxide, dimethylformamide, dimethylacetamide, dimethyllaurylamide, isosorbitol, olive oil, castor oil, squalene, and lanolin etc.; viscosity enhancers such as cellulose acetate, methyl cellulose, hydroxylmethyl cellulose, hydroxypropylemethyl cellulose, sodium carboxymethyl cellulose, stearyl alchohol etc; stimulant reducers such as glycerine mono-oleic acid, glycerine monolaurate, sorbitan monolaurate etc.; hydrophilic and water absorbing macromolecular substances such as karaya gum, tragacanth gum, polyvinyl alcohol and its partial saponified compounds, dextrin, albumin, polyamino acid, polyvinyl pyrrolidone, poly(meta) acrylate, polyacrylic acid and its sodium salt, polyacrylamide and their local hydrolytic products; plasticizers such as glycerin.

These additives when applied to the respective medicinal substances in the appropriate types and concentrations, as determined by the acceptable pharmacological range, will prove an effective medical treatment.

To increase conductivity, electrolytes such as sodium chloride, sodium carbonate, and potassium citrate may be added as the need artses.

The iontophoresis electrode can utilize either anode or cathode according to the ionic property of the medicinal substances. Also, both anode or cathode can be used at the same time.

The iontophoresis electrode was connected to the current generator circuit and power supply but this current generator circuit and power supply can also be separated from the iontophoresis electrode and connected by means such as connecting code. Miniaturization can be achieved by integrating these components with the iontophoresis electrode.

When components are integrated with the electrode, an electric circuit in which light-weight power supply which can be sticked to mucous membrane, particularly oral mucous membrane, is installed internally, is utilized.

As power supply, any of small-size and light-weight cell can be used. For instance, the cells include manganese cells, alkali cells, lithium cells, unicad cells, silver oxide cells, mercury cells, air cells, alkali-manganese cells, and plastic cells. Plastic cells are formed into button shape or sheet.

The electrical circuit utilizes a conductive layer for current dispersion having anode and cathode with their respective donor device and reference device directly connected to the power supply, or incorporate a pulse generator device or a pulse depolarizing device etc.

The current required for the iontophoresis device is normally 0.001 to 10 mA/cm$^2$, and preferably 0.01 to 1.0 mA/cm2. The battery output is generally about 0.5 to 18 volts depending on the contact surface area of the membrane between the iontophoresis electrode, and preferably is 3 to 9 volts. Therefore when needed, several light-weight batteries can be provided or several sheet of cells can be stacked, or amplifying elements in chip form can also be used. Addition of a constant-current element or a light emitting diode to indicate power, is also allowed.

A pulse generator connected between donor device and the power supply, and a switch connected between donor device and reference device are utilized for depolarization.

The pulse generator can be used to provide either a periodic pulse or a non-periodic pulse as the treatment pulse, depending on the amount of medicinal polymer physiologically active substance to be administered and condition of the recipient of the medicine.

The pulse generator can also be provided with an output limiting circuit to limit the large peak current flowing during the treatment pulse rise and fall time.

The switch eliminates polarized voltage stored between donor device and reference device, in other words, in the mucous membrane such as the oral mucous membrane during the treatment pulse pause interval. To accomplish this, a transistor switch such as an FET (Field Effect Transistor) is preferably utilized.

A feedback mechanism can be installed in the iontorphoresis device to automatically control the output current while monitoring the condition of the recipient, when the recipient's condition varies according to the dosage of the physiologically active polymer medicinal substances or when the dosage of the medicinal substances must be regulated. For instance, particularly in the case of administering insulin, when the insulin dosage must be regulated according to the blood sugar value, a blood sugar sensor can be connected to the power supply, and a feedback mechanism installed to automatically limit the output current and output time according to the sensor output. This arrangement demonstrates an optimal method for administering of physiologically active polymer medicinal substances according to the condition of the recipient in a way previously impossible by conventional means.

The manufacturing method for the iontorphoresis electrode and the device of this invention using it, will be explained following, by an example suited for administration through the oral mucous membrane.

1) A medicinal substance mixed in a dried polymer fluid with water soluble and swelling properties is dissolved in a suitable solvent and quickly dried to form a film, or a polymer layer formed in a dried film state not containing any medicinal substance is then later attached at its surface to a medicinal substance, or a spacer layer is fabricated containing the medicinal substance on the donor device side.

2) A film-shaped, dried polymer layer with water soluble and swelling properties not containing a medicinal substance is fabricated on the reference device side of the spacer layer as described above in step 1).

3) Conductive layer for current dispersion for the donor device is laminated on the backing layer, and an electrode laminated piece is fabricated for the donor device.

4) Conductive layer for current dispersion for the reference device is laminated on the backing layer, and an electrode laminated piece is fabricated for the reference device.

5) A donor device is fabricated sticking the donor device spacer layer and donor device electrode laminated piece.

6) A reference device is fabricated sticking the donor device spacer layer and reference device electrode laminated piece. This is only one example of the manufacturing process and the order of the above listed process can be changed as needed for manufacture.

The donor device and reference device can be formed at the tip of the nipping tool as a clip or clamp. Thereby the medicinal layer containing polymer physiologically active compounds in a predetermined dosage can be securely fixed to the administering site in the oral cavity and the medicinal substances can be administered with no leaks. Resilient metal wire can be utilized for the clips, or resilient metal material or synthetic resin can also be utilized.

As a method for fixing the backing layer to the nipping part, joining with adhesive can be performed or hooking which can fix detachably the nipping part and donor device etc. can be utilized.

Besides the above nipping tool, the donor device and the reference device can be integrated into a concentric shape, or each of them can be formed independently and sticked to the administration site. In this case the adhesive layer should be provided on the upper surface of the spacer layer or medicinal substance layer.

Pressure sensitive adhesive or gel-like gluing agent will work satisfactorily in the adhesive layer. This pressure sensitive adhesive or gel-like gluing agent can support the iontophoresis electrode on the surface of the patient's buccal mucosa and when a notch is provided on the protective layer, the protective layer will break at the notch when peeled providing ample adhesive strength. These adhesives can be used as the physical characteristics of the skin and membrane allow. For instance, acrylic adhesives such as poly-(2-ethylhexylacrylate), methacrylic adhesives such as polybutylmetacrylate, silicon adhesives such as polydimethylsiloxane, rubber adhesives such as polyisoprene rubber, polyisobutylene rubber, polybutadiene rubber, natural rubber polyvinyl alcohol, gelatin, polyvinyl pyrrolidone, carboxyvinyl polymer, and poly-(sodium acrylate) and its crosslinked products, sodium alginate and its crosslinked products, cellulose derivatives etc. can be used.

Function

1) The iontophoresis electrode has a structure such that;
   a. When a dried polymer layer with water soluble and swelling properties is used as the spacer layer, the layer absorbs water and has ample sticking strength so that the electrode can be sticked to the mucous membrane without using joining tape previously used. In particular, when the iontophoresis electrode is sticked to the oral mucous membrane, the medicinal substances can be administered easily and effectively since the iontophoresis device is formed with a light-weight battery and electrical circuit that are installed outside of the oral cavity.
   b. When the iontophoresis electrode with segmented conductive layer for current dispersion is sticked to the oral mucous membrane, since a connection between each electrode is achieved by saliva absorption of the spacer layer consisting of a dried polymer layer with water soluble and swelling properties, an iontophoresis device can be formed with one iontophoresis electrode. The thickness of the spacer layer and the absorption of saliva are in direct proportion so that the iontophoresis electrode and device can be attached and maintained at a suitable dispensing site without coming loose by means of saliva absorption and by increasing or decreasing the thickness of the spacer cell
   c. The size of iontophoresis electrode and device using it are small and can be sticked to the mucous membrane without using adhesive tape so that the medicinal substances can be administered to a patient without giving unpleasantness.
   d. A spacer layer containing a medicinal substances is provided between the conductive layer for current dispersion and the oral mucous membrane, so that safety in regards to electrical stimulation of the oral mucous membrane is remarkably improved.
   e. Providing an ionic polymer layer in the spacer layer restricts electrophoretic migration of ions in the spacer and absorption layers due to ion emissions from the electrodes when power is applied. This means that movement of ionic medicinal substances is not interfered with, and medicine can be quickly absorbed into the body through the buccal mucosa. Migration of ionic medicinal substance towards the conductive layer for current dispersion is also prevented.
   f. When a medicinal substance such as peptide compounds that is physiologically active polymer substances are adhered to the outer surfaces of the spacer layer, and when the electrode is sticked to the oral mucous membrane, the medicinal substance which is dissolved in saliva, exists on the mucous membrane surface in high concentration, and is electrically absorbed in the body quickly. Further, since the medicinal substance is maintained in a dry state until being administered, its stability and storability are remarkably improved.
   g. When an ionic polymer layer is provided in the spacer layer; donor device, reference device or both donor device and reference device can be used according to the ionic property of the medicinal substances.
   h. When silver and silver-chloride is used as the conductive layer for current dispersion, electrolysis of the water and saliva can be inhibited and the electric current used more efficiently.

2) The iontophoresis device has a structure such that
   a. When a switch is provided between the donor device and reference device, for depolarization during the treatment pulse stop period, an iontophoresis voltage is applied intermittently to the oral mucous membrane. This inhibits electrical stimulation (irritation) to the oral mucous membrane and remarkablly improves stability.
   b. Medicinal substance with polymer such as physiologically active substances can be placed in the oral mucous membrane in high concentration by means of saliva, and iontophoresis ensures the medicinal substance will be quickly absorbed into the body.

BEST MODE FOR CARRYING OUT THE INVENTION

Figure 1A:
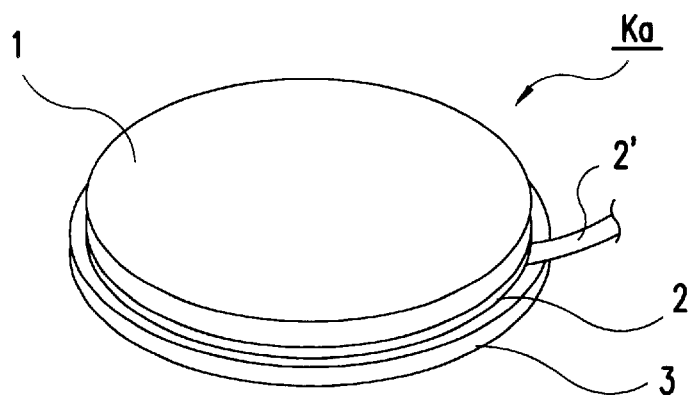
FIG. 1(a) is a perspective view of the iontophoresis electrode utilized on the donor device side in the first embodiment of this invention.

In following explanations of embodiments of the invention are given referring to the drawings.

Embodiment 1

Figure 1B:
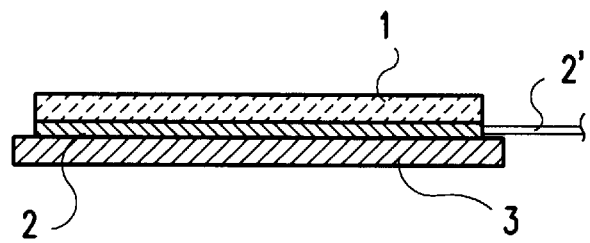
FIG. 1(b) is a principal part longitudinal cross sectional view of the center of the iontophoresis electrode utilized on the donor device side in the first embodiment of this invention.
Figure 1C:
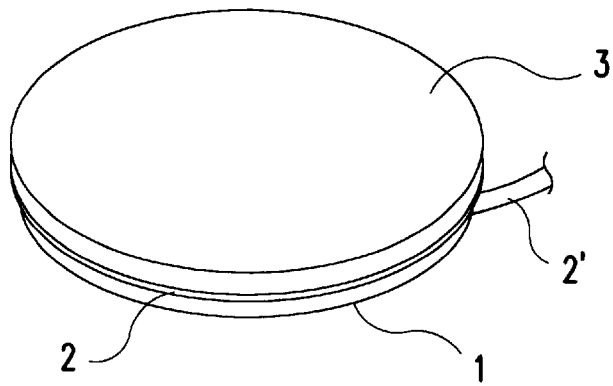
FIG. 1(c) is a perspective rear view of the iontophoresis electrode utilized on the donor device side in the first embodiment of this invention.

FIG. 1(a) is a perspective view of the iontophoresis electrode utilized on the donor device side. FIG. 1(b) is a principal part longitudinal cross sectional view of the center of that iontophoresis electrode. FIG. 1(c) is a perspective rear view.

The characters Ka indicate the iontophoresis electrode utilized on the donor device side. Reference numeral 1 denotes a backing layer formed in a disc shape from a polyolefin sheet or film such as polyester or polyethylene. Reference numeral 2 denotes a conductive layer for current dispersion formed by vapor deposition of silver on one surface of the backing layer 1. Reference numeral 2' denotes the lead wire connected to the conductive layer for current dispersion 2. Reference numeral 3 denotes a spacer layer laminated on conductive layer for current dispersion 2 and made of dried polymer layer with water soluble and swelling properties of sodium alginate, polyvinyl alcohol, or chitin etc. containing the medicinal substances formed 1.01 to 1.3 times the diameter of the conductive layer for current dispersion 2.

The iontophoresis electrode of this embodiment, formed as described above can thus start absorption of saliva simultaneous with attachment of the spacer layer to the oral mucous membrance and further attach while swelling. The medicinal substances are dissolved by the saliva, the expansion of the spacer layer increases the surface area for administration of the medicine and the efficiency of the administration of the medicine is further improved.

Figure 2A:
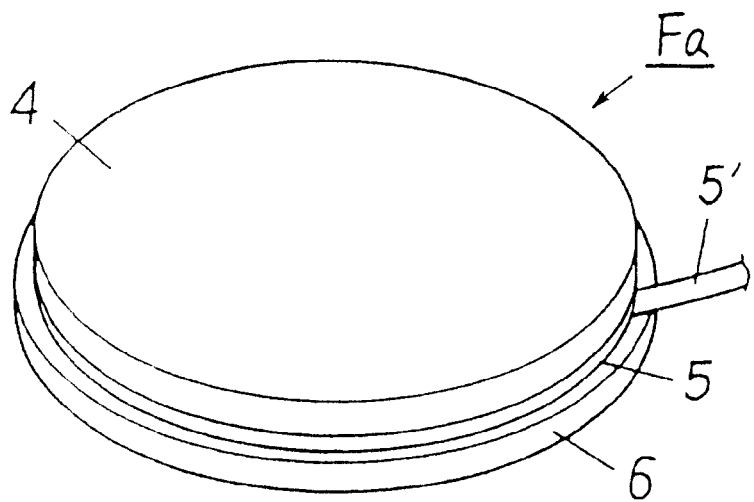
FIG. 2(a) is a perspective view of the iontophoresis electrode utilized on the reference device side in the first embodiment of this invention.
Figure 2B:
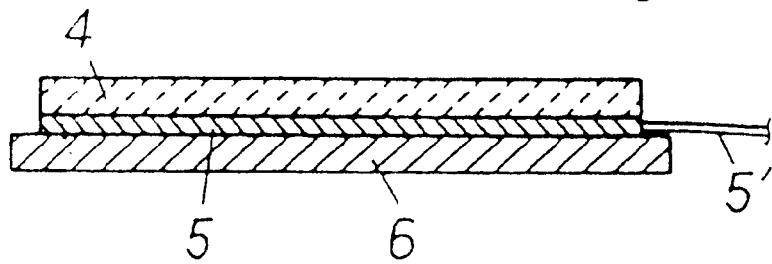
FIG. 2(b) is a principal part longitudinal cross sectional view of the center of the iontophoresis electrode utilized on the reference device side in the first embodiment of this invention.

FIG. 2(a) is a perspective view of the iontophoresis electrode utilized on the reference device side in the first embodiment of this invention. FIG. 2(b) is a principal part longitudinal cross sectional view of the center of the iontophoresis electrode.

In the drawing, the characters Fa denote the iontophoresis electrode on the reference device side in the first embodiment. Reference numeral 4 denotes the backing layer made of the same configuration and material as donor device Ka. Reference numeral 5 denotes the conductive layer for current dispersion made from silver chloride leaf processed with hydrochloric acid after vapor deposition of silver on the support layer 4. Reference numeral 5' is the lead wire. Reference numeral 6 denotes the spacer layer made of dried polymer film with water soluble and swelling properties with a size and material identical to the donor device side but containing no medicinal substances. The iontophoresis device is thus configured as described above, utilizing iontophoresis electrode on the donor device side and reference device side.

Figure 3:
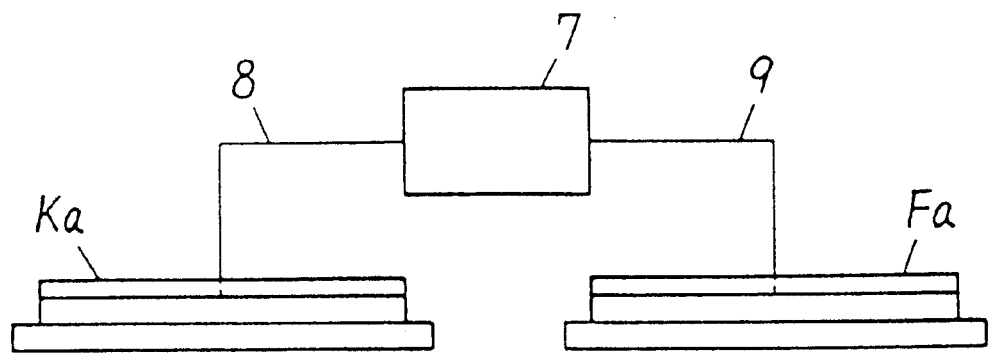
FIG. 3 is a model view of the iontophoresis device used in the iontophoresis electrode in the first embodiment of this invention.

FIG. 3 is a model view of the iontophoresis device used in the iontophoresis electrode in the first embodiment of this invention.

Figure 4:
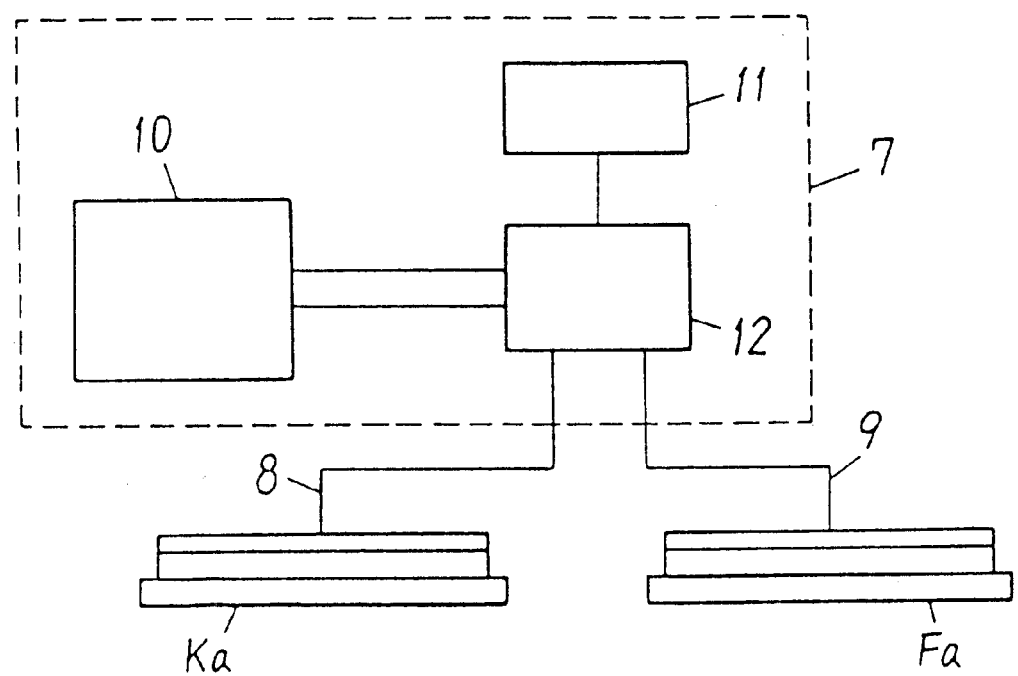
FIG. 4 is a model view of the electrical circuit of the iontophoresis device used in the iontophoresis electrode in the first embodiment of this invention.

FIG. 4 is a model view of the electrical circuit of the iontophoresis device.

In FIG. 3, reference numeral 7 denotes an electrical circuit as a current adjusting means consisting of a power supply for supplying a constant DC current or DC pulse current using a small size cell, a switching means for turning on and off the power, a current regulator for generating a DC current or DC pulse current and for reversing the polarity of both electrodes at specified times, and a resistor as a current limiting device to prevent excess current for maintenance of safety. Reference numerals 8 and 9, respectively, denote lead wires for connecting the donor device Ka, the reference device Fa and electrical circuit 7. In FIG. 4, reference numeral 10 is a constant DC power supply. 11 is a timer. Reference numeral 12 denotes a switching section for switching polarity of each voltage applied to the donor device Ka and the reference device element Fa at specified time in a linked operation with the timer 11.

Therefore, in the iontophoresis device of the first embodiment, when the iontophoresis electrodes in the donor device and reference device side are sticked to the oral mucous membrane, dried polymer film with water soluble and swelling properties of the spacer layers in both sides absorbs saliva, and the result, the iontophoresis electrodes in both sides can form a closed circuit through the oral mucous membrane.

Embodiment 2

Figure 5A:
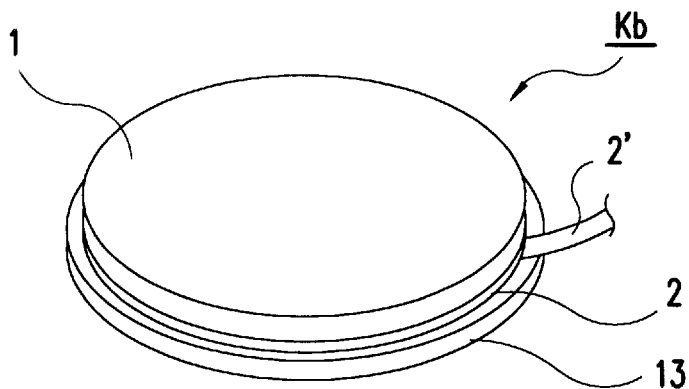
FIG. 5(a) is a perspective view of the iontophoresis electrode utilized on the donor device side in the second embodiment of this invention.
Figure 5B:
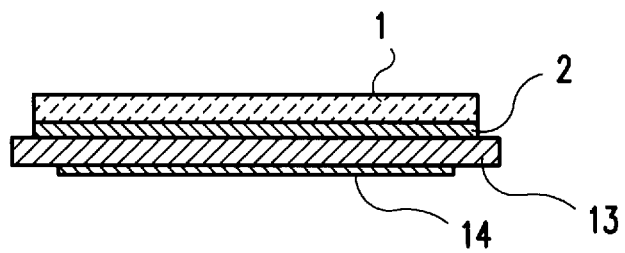
FIG. 5(b) is a principal part longitudinal cross sectional view of the center of the iontophoresis electrode utilized on the donor device side in the second embodiment of this invention.
Figure 5C:
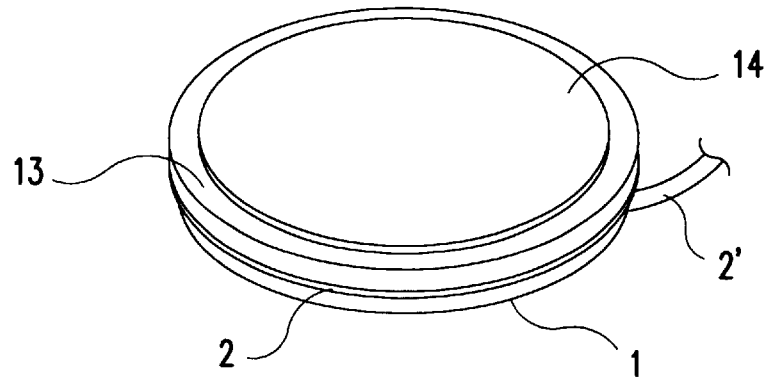
FIG. 5(c) is a perspective rear view of the iontophoresis electrode utilized on the donor device side in the second embodiment of this invention.

FIG. 5(a) is a perspective view of the iontophoresis electrode utilized on the donor device side in the second embodiment of this invention. FIG. 5(b) is a principal part longitudinal cross sectional view of that center. FIG. 5(c) is a perspective rear view.

The difference between the Kb iontophoresis electrode on the donor device side in the second embodiment and the Ka electrode in the donor device side in the first embodiment, is that medicinal substances 14 consisting of specified amounts of peptide compounds of polymer physiologically active agents are sticked to the top surface of the spacer layer 13.

The iontophoresis electrode on the reference device side can be used in the same as that in the first embodiment, so that its explanation will be omitted.

Therefore, in the iontophoresis electrode of this embodiment, absorption of saliva starts at the same time that the medicinal substance 14 on the outermost surface of the spacer 13 is attached to the oral membrane. This allows the medicinal substance 14 of peptide compounds of polymer physiologically active agents to be efficiently absorbed directly into the circulating blood. The spacer layer 13 is formed larger than the conductive layer for current dispersion 2 so that the direct contact of the conductive layer for current dispersion 2 with the oral mucous membrane to which the medicinal substance is administered, is prevented, and the electrical stimulation (irritation) to the mucous membrane can be kept extremely low.

The iontophoresis electrode of this embodiment was formed larger than the conductive layer for current dispersion but when the electrode is large, the electrode may be formed to nearly the same size (1.01 times) as the conductive layer for current dispersion in order to reduce a feel of physical disorder in the oral cavity.

Embodiment 3

The iontophoresis electrode of the third embodiment was fabricated utilizing non-woven fabric as the spacer layer, silver for the anode and silver chloride for the cathode as the conductive layer for current dispersion and salmon calcitonin as the medicinal substance in the structure of the iontophoresis electrode described in the second embodiment. A power supply connected on the now fabricated iontophoresis device and the device was administered to the oral mucous membrane of a dog. Tests were performed applying six volt supplied by an external power supply. After two hours elapsed after the start of testing, an evaluation of the electrical stimulation was performed by observation of the change of administration site. Evaluation was performed by comparing changes of the administration site with those of non-administration site. Changes such as flare were labeled [STIMULATION] and no changes were labeled [NO STIMULATION]. These test results are shown in Table 1.

Embodiment 4

The iontophoresis electrode of the fourth embodiment was fabricated, using PVA gel as the spacer layer, titaniums for the anode and the cathode as the conductive layer for current dispersion and insulin as the medicinal substance in the structure of the iontophoresis electrode described in the second embodiment. The test was performed with the same condition done in the third embodiment except applying eight volt. The test results are shown in Table 1.

Comparision Example 1

A conductive layer for current dispersion was attached directly to the oral mucous membrane without laminating a spacer layer. As the conductive layer for current dispersion, silver was used in the anode and silver chloride for the cathode and other conditions were identical to those of the third embodiment. These test results are shown in Table 1.

As clearly shown by the results in Table 1, no changes were found in the administration sites in the third and fourth embodiments but in the Comparison Example 1 which had no spacer layer, flares were found, suggesting that the iontophoresis voltage was stimulating (irritating) the membrane.

Embodiment 5

The iontophoresis electrode of the fifth embodiment was fabricated using PVA gel as the spacer layer, titaniums for the anode and the cathode as the conductive layer for current dispersion and insulin as the medicinal substance in the structure of the iontophoresis electrode described in the second embodiment. The test was performed with the same condition done in the third embodiment except applying eight volt. The test results are shown in Table 1.

Embodiment 6

The iontophoresis electrode of the sixth embodiment was fabricated using hydroxypropylmethylcellulose (HMPC) as the spacer layer, silver for the anode and silver chloride for the cathode as the conductive layer for current dispersion in the structure of the iontophoresis electrode described in the second embodiment. The test was performed with the same condition done in the fifth embodiment except applying six volt. The test results are shown in Table 1.

Comparison Example 2

A conductive layer for current dispersion was sticked directly to the oral mucous membrane without laminating a spacer layer. As the conductive layer for current dispersion, titanium was used in both the anode and cathode and other conditions were identical to the fifth embodiment. These test results are shown in Table 1.

As clearly shown by the results in Table 1, no changes were found in the administration sites in the fifth and sixth embodiments which had a spacer layer to prevent direct contact with the oral mucous membrane and so electrical stimulation (irritation) could be reduced to an extremely low level. In contrast, in the Comparison Example 2 which had no spacer layer, flares were found at contact site with the oral membrane, demonstrating that the stimulation of the membrane was quite severe.

Embodiment 7

Figure 6A:
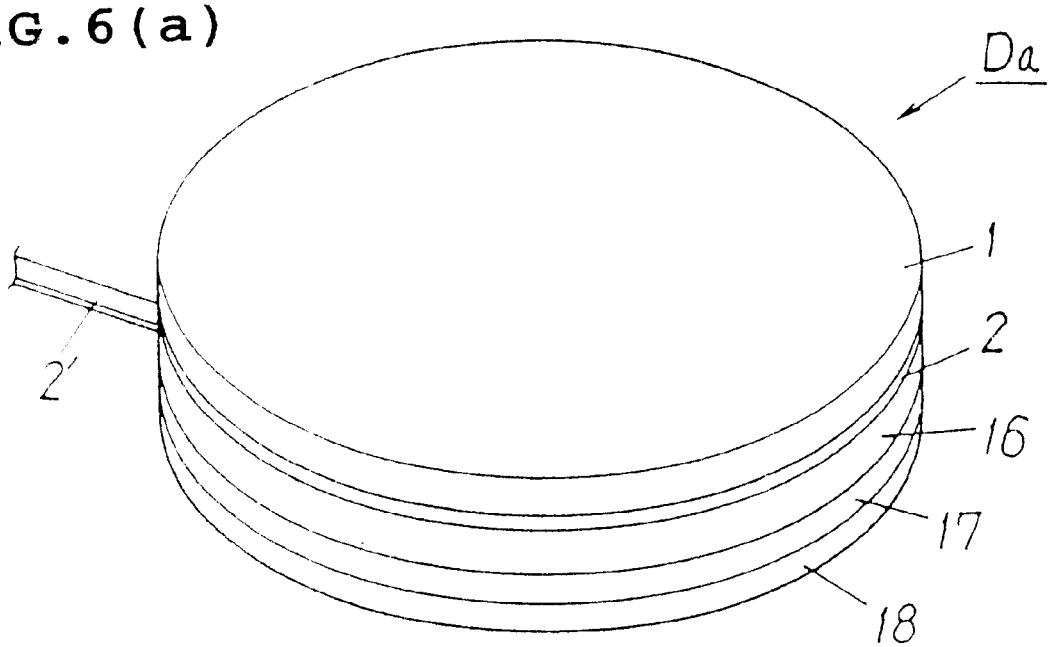
FIG. 6(a) is a perspective view of the iontophoresis electrode utilized in the seventh embodiment of this invention.
Figure 6B:
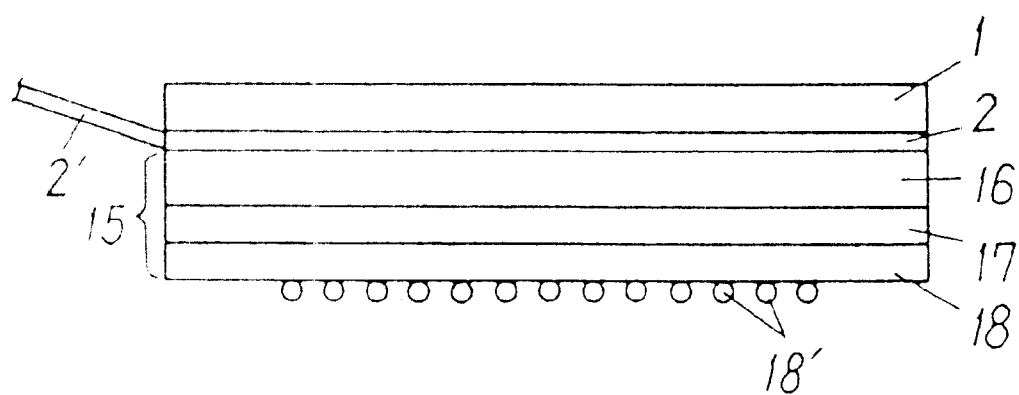
FIG. 6(b) is a principal part longitudinal cross sectional view of the center of the iontophoresis electrode utilized in the seventh embodiment of this invention.

FIG. 6(a) is a perspective view of the iontophoresis electrode utilized in the seventh embodiment of this invention. FIG. 6(b) is a principal part longitudinal cross sectional view of that center.

In the figure, the characters Da denote the iontophoresis electrode of the seventh embodiment for administering the medicinal substances to the buccal. Reference numeral 1 denotes a backing layer formed as a sheet or film of polyolefin such as polyester or polyethylene. Reference numeral 2 denotes a conductive layer for current dispersion formed by deposition of silver on one surface of the backing layer 1. Reference numeral 2' denotes the lead wire connected to the conductive layer for current dispersion 2. Reference numeral 15 denotes a spacer layer integrally laminated with medicinal substance layer 18, ionic polymer layer 17, and water absorbing layer 16 and laminated on conductive layer for current dispersion 2.

Here, the water absorbing layer 16 is formed of polyvinyl alcohol etc. The ionic polymer layer 17 is formed of a styren-divinyl benzen copolymer containing amino ternary as the ion exchange group. The medicinal substance layer 18 is formed of non-woven fabric. The medicinal substance 18' is calcitonin adhered in a dry state to the outermost layer of the medicinal substance layer 18.

Therefore, in the iontophoresis electrode of this embodiment, a spacer layer 15 attached with the medicinal substance 18' on the outermost surface, between conductive layer for current dispersion 2 and the oral membrane, allowing the stimulation of the oral mucous membrane to be limited. Also, the medicinal substance 18' on the outermost surface of spacer layer 15, in other words the outermost layer of the medicinal substance layer 18, is dissolved by the saliva simultaneous with attachment to the oral mucous membrane permitting effective direct absorption into the blood circulation. The presence of the ionic polymer layer 17 inside the water absorbing layer 16, permits medicinal substance 18' ions to move freely without any movement interference. Further, migration of ionic medicine towards the conductive layer for current dispersion 2 is prevented, so the ionic medicine can move freely towards the oral mucous membrane.

Embodiment 8

The donor device of the seventh embodiment was utilized as the oral administration iontophoresis electrode of the eighth embodiment, and silver chloride was used for the reference device as the conductive layer for current dispersion. Stimulation (irritation) tests were then performed by administering medicine to the oral mucous membranes of a beagle dog. Tests were performed with an iontophoresis voltage of six volt from an external power supply.

An evaluation of the electrical stimulation was performed by observation applicable changes at administration site after two hours elapsed after the start of testing and by comparing changes of the administration site with those of non-administration site. Changes such as flare were labeled [STIMULATION] and no changes labeled [NO STIMULATION]. These test results are shown in Table 2.

Embodiment 9

The iontophoresis electrode for administration to the oral mucous membrane of ninth embodiment was fabricated just as for the eighth embodiment except that no ionic polymer layer was prepared. Tests were performed under conditions identical to those of the eighth embodiment. These test results are shown in Table 2.

Comparison Example 3

The iontophoresis electrode for administration to the oral mucous membrane of Comparison Example 3 was fabricated just as for the eighth embodiment except that no spacer layer (namely an water absorbing layer, ionic polymer layer, and medicinal substance layer) was prepared. Tests were performed under conditions identical to those of the eighth embodiment. These test results are shown in Table 2.

As Table 2 clearly shows, no evidence of electrical stimulation (irritation) was found in the eighth and ninth embodiments. In contrast, however, the Comparison Example 3 showed strong electrical stimulation, indicating that safety was inadequate.

Embodiment 10

Figure 7A:
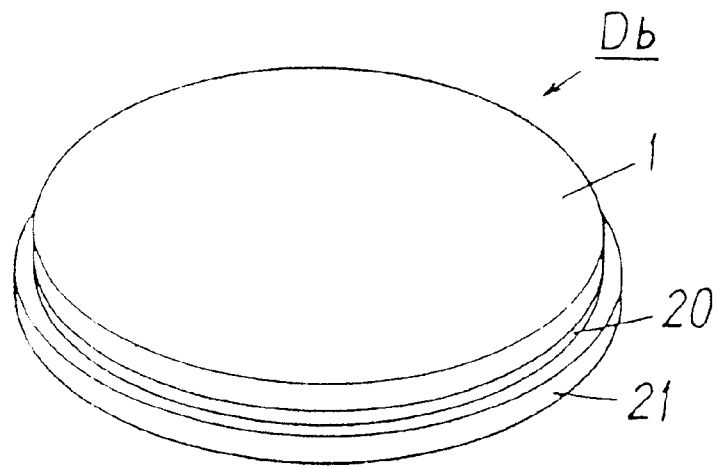
FIG. 7(a) is a perspective view of the iontophoresis device utilized in the tenth embodiment of this invention.
Figure 7B:
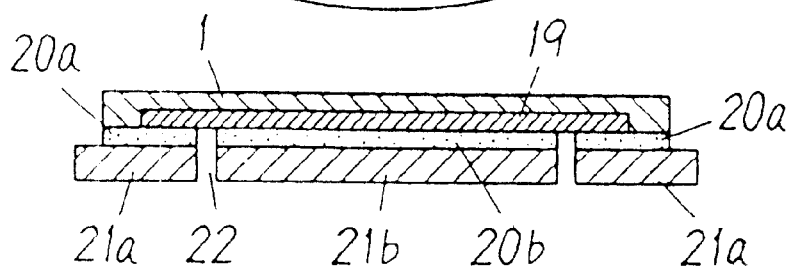
FIG. 7(b) is a principal part longitudinal cross sectional view of the center of the iontophoresis device utilized in the tenth embodiment of this invention.
Figure 7C:
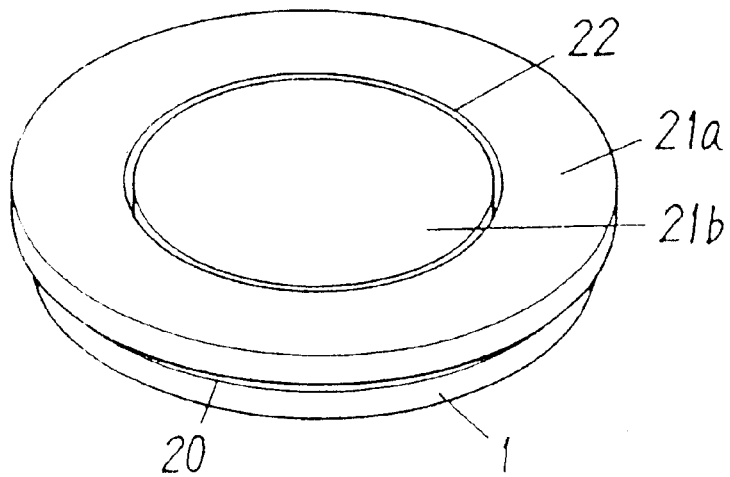
FIG. 7(c) is a perspective rear view of the iontophoresis device utilized in the tenth embodiment of this invention.

FIG. 7(*a*) is a perspective view of the iontophoresis device utilized in the tenth embodiment of this invention, with the donor device and reference device integrated into one body. FIG. 7(*b*) is a principal part longitudinal cross sectional view of its center. FIG. 7 (c) is a perspective rear view. In the drawings, the characters Db denote the iontophoresis device of the tenth embodiment. Reference numeral 1 denotes the backing layer. Reference numeral 19 denotes the electrical circuit part with a light-weight cell of the button-shaped type, installed in the inner surface of the backing layer 1. Reference numeral 20 denotes the conductive layer for current dispersion formed in a segmented and separated concentric shaped disks to contact anode and cathode of the button-shaped cell and the backing layer 1. Reference numerals 20*a* and 20*b* denote the conductive layer for current dispersion of the donor and reference device. Reference numeral 21 is the spacer layer formed of dried polymer film with water soluble and swelling properties and laminated with the conductive layer for current dispersion which is concentric shaped disks 20*a* and 20*b*. Reference numeral 21*a* denotes the spacer layer for the reference device side. Reference numeral 21*b* denotes the spacer layer for the donor device side coated with insulin. Reference numeral 22 denotes the insulator for electrically insulating the conductive layer for current dispersion for the reference device side 20*a*, and the conductive layer for current dispersion for the donor device side 20*b*.

The configuration of the backing layer 1, the conductive layer for current dispersion 20 and the spacer layer 21 is largely the same as that of the first embodiment, so that its explanation will be omitted here.

The operation of the iontophoresis device of the tenth embodiment described above is as follows.

The spacer layers 21*a* and 21*b* attached to the oral mucous membrane, swell as saliva is soaked up, forming a strong connection to the oral mucous membrane. The attached Db iontophoresis device forms an electrical closed circuit when the saliva causes an electrical connection between the conductive layers for current dispersion 20*a* and 20*b*.

The device of this embodiment configured as above is light-weight with donor and reference device integrated into one body so that the iontophoresis device can be easily installed even on narrow mucous membrane such as buccal.

In this embodiment, the donor device was placed in the center and the reference device on the periphery, although this can be interchanged if desired, by placing the reference device in the center and the donor device on the periphery.

Embodiment 11

Figure 8A:
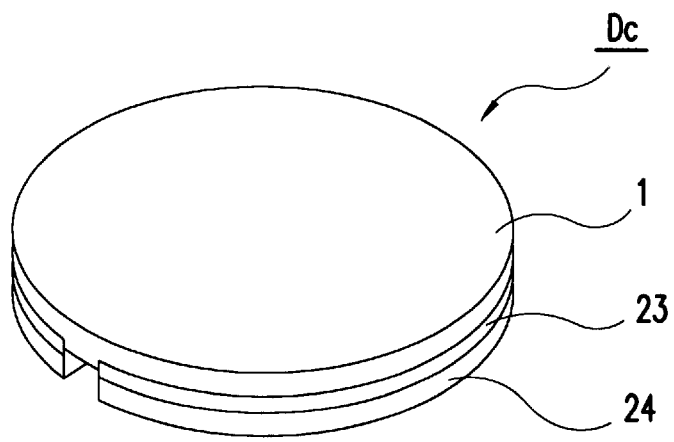
FIG. 8(a) is a perspective view of the iontophoresis device utilized in the eleventh embodiment of this invention.
Figure 8B:
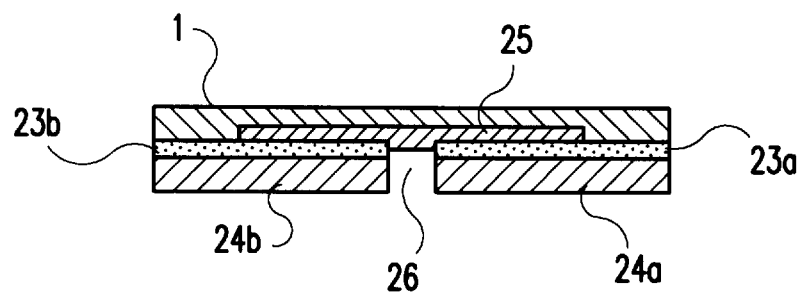
FIG. 8(b) is a principal part longitudinal cross sectional view of the center of the iontophoresis device utilized in the eleventh embodiment of this invention.
Figure 8C:
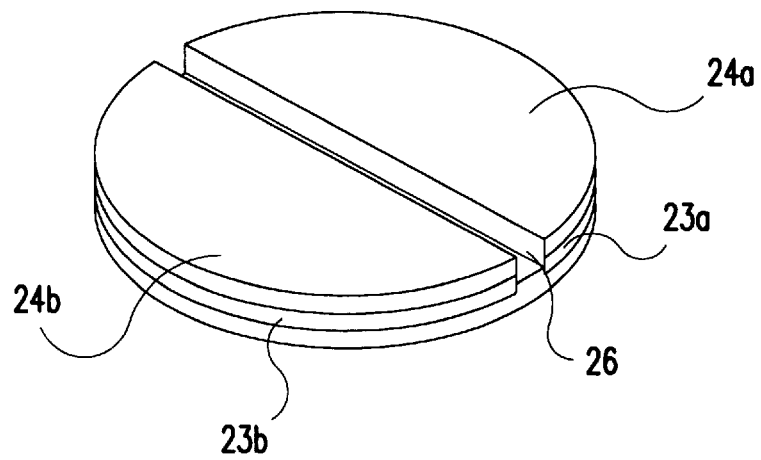
FIG. 8(c) is a perspective rear view of the iontophoresis device utilized in the eleventh embodiment of this invention.

FIG. 8(*a*) is a perspective view of the iontophoresis device utilized in the eleventh embodiment of this invention. FIG. 8(*b*) is a principal part longitudinal cross sectional view of its center. FIG. 8 (c) is a perspective rear view.

In the drawings, the character Dc denote the iontophoresis device of the eleventh embodiment. Reference numeral 1 denotes the backing layer. Reference numeral 23 denotes the conductive layer for current dispersion segmented into two pieces; the donor device side 23a and the reference device side 23b. Reference numeral 24 is the spacer layer formed of dried polymer film with water soluble and swelling properties and laminated with the conductive layer for current dispersion for donor device side 23a and the reference device side 23b. Reference numeral 24a is the spacer layer on the donor device side containing the medicinal substances, and 24b is the spacer layer for the reference device side. Reference numeral 25 is the light-weight, circuit and sheet-shaped cell which anode and cathod were connected to the conductive layer for current dispersion 23b of reference device side and the conductive layer for current dispersion 23a of donor device according to the ionization of the medicine installed in the back side of the backing layer 1. Reference numeral 26 denotes the insulator for electrically insulating the conductive layer for current dispersion for the reference device and conducting element sides.

This embodiment configured as above is light-weight with donor and reference device integrated into one body so that not only the iontophoresis device can be easily installed even on narrow mucous membrane such as buccal but also the dried polymer with water soluble and swelling properties is separated into a semi-circular shape for easy attachment.

Embodiment 12

Figure 9:
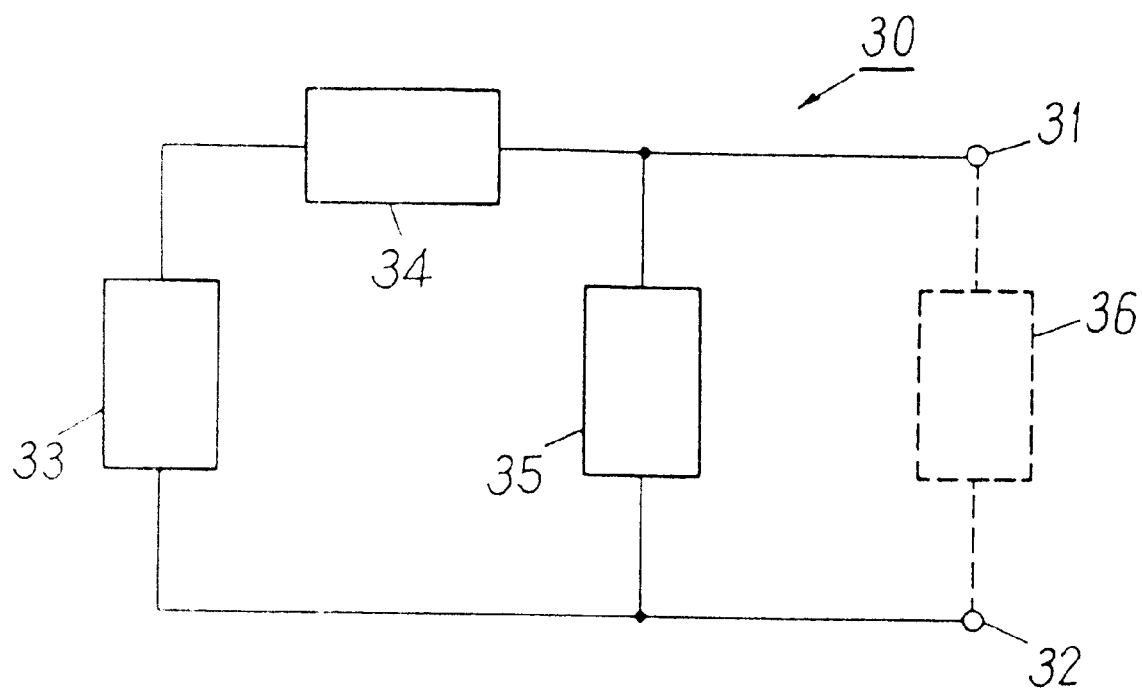
FIG. 9 is a circuit model view showing the iontophoresis device for oral mucous membranes used in the twelth embodiment of this invention.
Figure 10A:
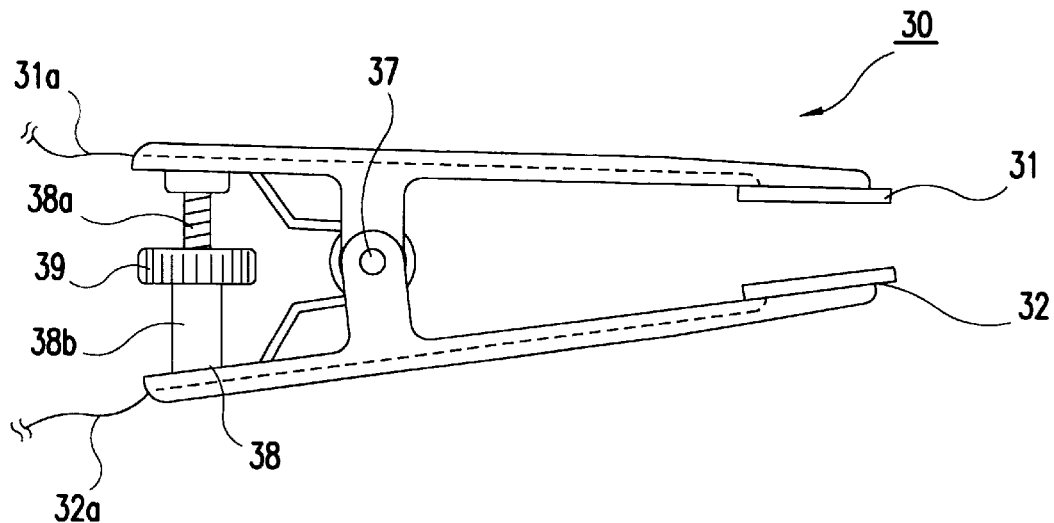
FIG. 10(a) is a principal part top plan view of the iontophoresis device for oral mucous membranes used in the twelth embodiment of this invention.
Figure 10B:
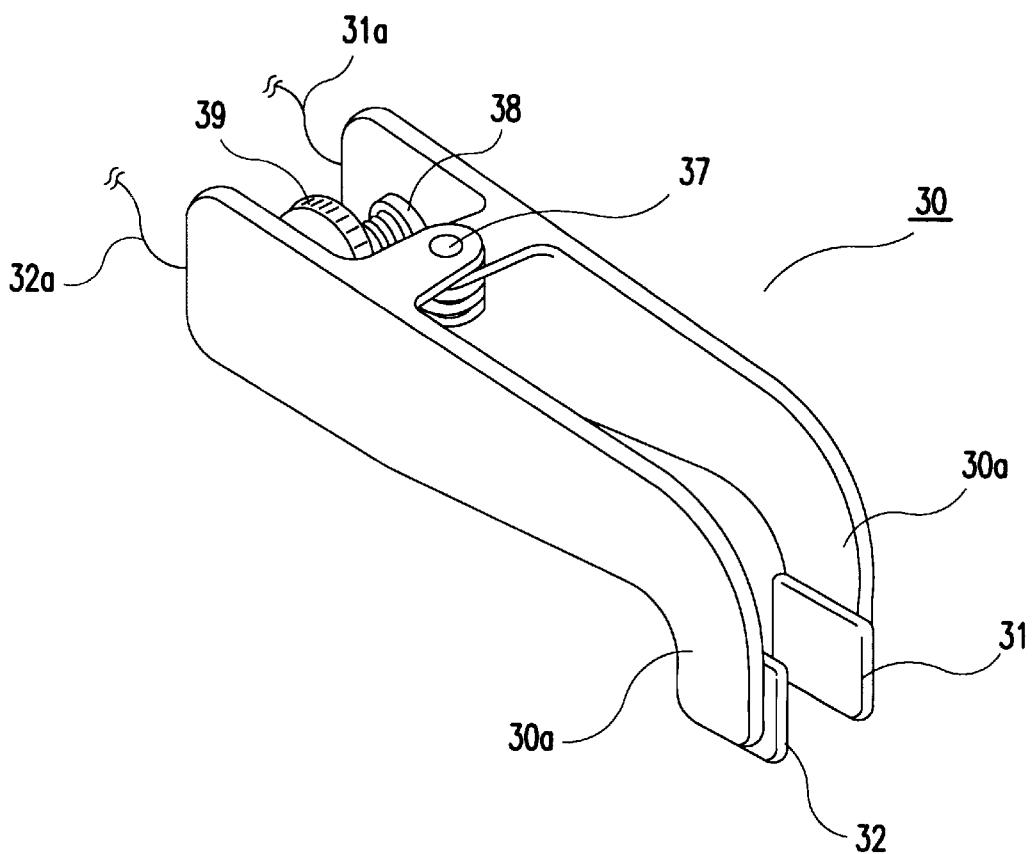
FIG. 10(b) is a principal part perspective view of the iontophoresis device for oral mucous membranes used in the twelfth embodiment of this invention.

FIG. 9 is a circuit model view showing the iontophoresis device for oral mucous membranes used in the twelfth embodiment of this invention. FIG. 10(*a*) is a top plan view of the iontophoresis device formed in a clip state for oral mucous membrane administration. FIG. 10(*b*) is a principal part perspective view.

Reference numeral 30 denotes the iontophoresis device of the twelfth embodiment. Reference numeral 31 denotes a donor device containing the medicine which is a physiologically active agent. Reference numeral 32 denotes a reference device. Reference numeral 33 denotes a power supply such as a cell for applying a current/voltage between the conductive layers for current dispersion for the donor device 31 and the reference device 32. Reference numeral 34 denotes a pulse generator for generating a DC pulse of about 1,000 Hz to 100 kHz. Reference numeral 35 denotes a switch for depolarizing polarized voltage of donor device 31 and reference device 32 simultaneous with the pause in the treatment pulse voltage output from the pulse generator 34. Reference numeral 36 denotes a medicinal administration site such as the oral mucous membrane of a human.

In FIG. 10(*a*) and(*b*), reference numerals 31a and 32a are lead wires to connect donor device 31 and reference device 32 to the power supply 33 etc. The reference number 37 is a spring made of a resilient material such as a coil spring to provide support to the donor device 31 and reference device 32 attached to the oral mucous membrane. The reference number 38 is an opening adjuster to adjust the opening of the donor device 31 and reference device 32 at the screw mating section 39 with the female screw 38a and the male screw 38b.

The donor device and reference device are described next.

Figure 11A:
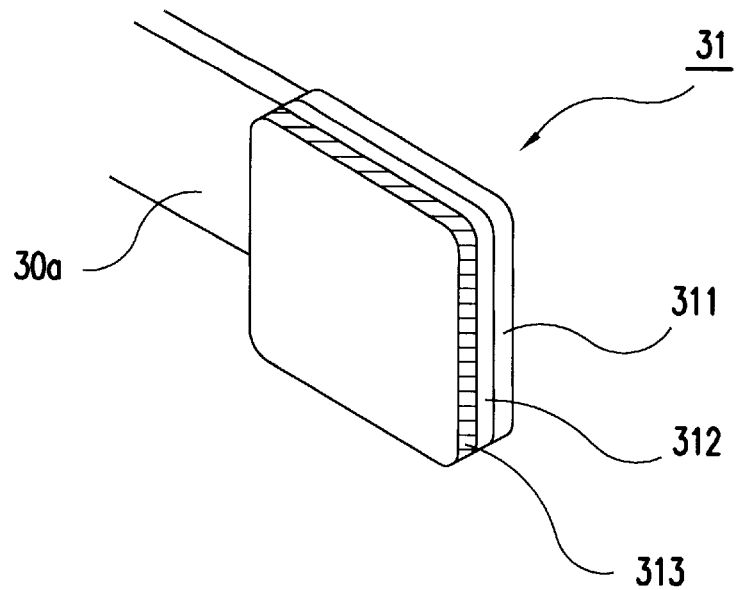
FIG. 11(a) is a perspective view showing the reference device fixed to the iontophoresis device for oral mucous membranes in the twelfth embodiment of this invention.
Figure 11B:
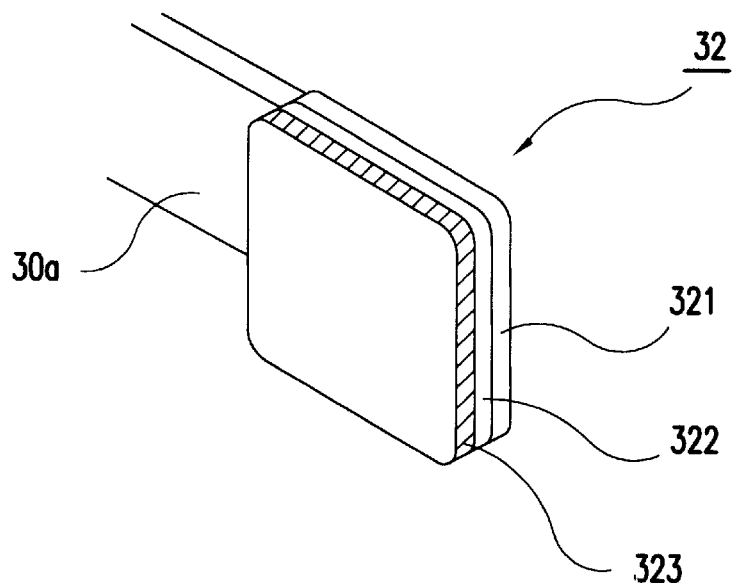
FIG. 11(b) is a perspective view showing the reference device fixed to the iontophoresis device for oral mucous membranes in the twelfth embodiment of this invention.

FIG. 11(*a*) is a perspective view showing the reference device fixed to the iontophoresis device for oral mucous membranes in the twelfth embodiment. FIG. 11(*b*) is a perspective view showing the reference device fixed to the iontophoresis device for oral mucous membranes.

The reference number 311 is a backing layer bonded with an adhesive agent etc. to the inner side of the edge of the support piece 30a of one side of the iontophoresis device 30 for oral mucous membrane. Reference numeral 312 denotes the conductive layer for current dispersion formed on the inner side of the backing layer 311. Reference numeral 313 is the spacer layer on the donor device 31 side for dispersion or attachment of a medicinal polymer substance such as physiologically active agents to non-woven fabric formed of soft materials. Reference numeral 321 is a backing layer fixed and facing donor device 31 at the edge of the support piece 30a on the other side of the iontophoresis device 30. Reference numeral 322 is a conductive layer for current dispersion formed on the inner side of the backing layer 321. Reference numeral 323 is a spacer layer on the reference device 32 side, material that is soft and swells up by absorption of saliva such as conductive gel.

The iontophoresis device of the twelfth embodiment for oral mucous membrane in this invention, configured as described above, is operated as follows.

The space between donor device and reference device is set just wider than the thickness of cheak membrane with screwing the section 40 of the iontophoresis clamp 37a for buccal application in this study. Next, the donor device 31 and reference device 32 are placed on both the oral mucous membrane and cheek surfaces, opening of the screw mating section 39 is adjusted and it is fastened to the administration site. The spacer layer 313 and the spacer layer 323 are made of soft material and so will not cause pain to the patient when clamped. Next, the power supply is turned on and the frequency and treatment pulse voltage output time of the pulse generator 34 are adjusted. The switch 35 is turned on and the measured dose of medicine is administered. After administering the dose, the switch 35 is turned off, the screw mating section 39 is rotated and the donor device 31 and reference device 32 are removed from the administration site so as to finish the treatment process.

The iontophoresis device of this embodiment, formed as described above can thus form a closed electrical circuit with the donor device and reference device of the iontophoresis electrode when these electrodes are sticked to the oral mucous membrane because both the spacer layers soak up the saliva in the oral mucous membrane, and become conductive to complete an electrical circuit to the electrodes via the donor device and reference device. The support means provided by the clamp for the donor device and reference device at the medicine administration site allows fastening of the attachment during the interval the medicine is being administered so that the donor device will not come loose, and the medicine of polymer material such as physiologically active agents can be administered smoothly.

In regards to the clamp used, items other than the example in this embodiment can be used such as direct or reverse grips or bulldog forceps etc. By changing the shape and length of these clamps as required by the medicine administration site, a reliable attachment can be made at the administration site inside the oral cavity or other locations, not only for just humans but also for other animals such as cats or dogs.

Embodiment 13

In the iontophoresis device of the twelfth embodiment, the reference device and donor device of the iontophoresis electrode were formed with silver in the anode and silver chloride in the cathode as the conductive layer for current dispersion. Salmon calcitonin was the medicine of polymer material having physiologically active agents, in the donor device. This was then administered to the oral membrane of a dog by iontophoresis. Tests were performed using a depolarizing type pulse generator utilizing a six volt iontophoresis voltage. At a specified time after starting the experiment, an evaluation of the electrical stimulation was performed by observation of the change of administration site. Evaluation was performed by comparing changes of the administration site with those of non-administration site. Changes such as flare were labeled [STIMULATION] and no changes were labeled [NO STIMULATION]. These test results are shown in Table 3.

Embodiment 14

In the iontophoresis device of the twelfth embodiment, the iontophoresis electrodes were fabricated with carbon for the anode and cathode as the conductive layer for current dispersion. Salmon calcitonin was administered with an eight volt iontophoresis voltage and tests were performed under conditions identical to those of the thirteenth embodiment. These test results are shown in Table 3.

Comparison Example 4

A constant DC power supply was used with the iontophoresis device of the twelfth embodiment. Other than applying a current of 3 milliamperes, the test was carried out under conditions identical to those of the thirteenth embodiment. These test results are shown in Table 3.

Comparison Example 5

In the iontophoresis device of the twelfth embodiment, other than using a non-polarizing pulse generator, the test was carried out under conditions identical to those of the thirteenth embodiment. These test results are shown in Table 3.

The calcitonin concentration in the blood was detected in all cases, although as shown in Table 3, stimulation (irritation) was found in the oral mucous membranes in medicine dispensing sites for both Comparison Example 1 and Comparison Example 2. In contrast, no signs of stimulation (irritation) were found at medicine administration sites in the thirteenth and fourteenth embodiments.

Embodiment 15

In the iontophoresis device of the twelfth embodiment, the reference device and donor device of the iontophoresis electrode were formed with silver in the anode and silver chloride in the cathode as the conductive layer for current dispersion. Insulin was the medicine of polymer material having physiologically active agents in the donor device. This was then administered to the oral mucous membrane of a dog by iontophoresis. Tests were performed with a depolarizing type pulse generator utilizing a six volt iontophoresis voltage. At a specified time after the starting the experiment, an evaluation of the electrical stimulation was performed by observation of the change of administration site. Evaluation was performed by comparing changes of the administration site with those of non-administration site. Changes such as flare were labeled [STIMULATION] and no changes were labeled [NO STIMULATION]. These test results are shown in Table 4.

Embodiment 16

In the iontophoresis device of the twelfth embodiment, the iontophoresis electrodes were fabricated with titanium for the anode and cathode as the conductive layer for current dispersion. Insulin was administered with an eight volt iontophoresis voltage and tests were performed under conditions identical to those of the fifteenth embodiment. These test results are shown in Table 4.

Comparison Example 6

A constant DC power supply was used with the iontophoresis device of the twelfth embodiment. Other than applying a current of 3 milliamperes, the test was carried out under conditions identical to those of the fifteenth embodiment. These test results are shown in Table 4.

Comparison Example 7

In the iontophoresis device of the twelfth embodiment, other than using a non-polarizing pulse generator, the test was carried out under conditions identical to those of the fifteenth embodiment. These test results are shown in Table 4.

The glucose concentration in the blood was detected in all cases for both the sixteenth and seventeenth embodiments quickly after administration of the dose. However, as shown in Table 4, stimulation (irritation) was found in the oral mucous membranes in medicine administration sites for both Comparison Example 6 and Comparison Example 7. In contrast, no signs of stimulation (irritation) was found at medicine administration sites in the sixteenth and seventeenth embodiments.

INDUSTRIAL APPLICABILITY

The iontophoresis electrode and a device using this iontophoresis electrode as described above have the following superior effects and attain the objective of providing an excellent medical treatment allowing full benefit to be obtained from the effective pharmaceutical products used in the medical field.

(1) Effect of the Iontophoresis Electrode a. A spacer layer containing the medical substance is provided between the conductive layer for current dispersion and the oral mucous membrane so that not only is the medicinal substance efficiently absorbed into the body, but also the safety of the electrical stimulation of the oral mucous membrane has been remarkably improved.

b. The medicinal substance is attached to the outermost surface of the spacer so that the medicinal substance is dissolved by the saliva simultaneous with attachment of the iontophoresis electrode to the oral membrane. The ionic medicinal substance is present with high concentration at the surface of the oral mucous membrane so that the medicinal substance can be absorbed easily, the discharge of the medicine is excellent, and physiologically active peptide compounds is directly and efficiently absorbed into the blood circulatory system.

Also, the medicinal substance is maintained in the spacer layer or medicinal substance layer in a dried state so that the medicine is extremely stable over the passage of time.

c. A dried polymer layer with water soluble and swelling properties is provided as the spacer layer so that during use, this polymer layer absorbs the body fluid or saliva, expands and seals itself to the oral mucous membrane, by just attaching it to the membrane when needed.

d. An ionic polymer layer is provided in the spacer layer so that the medicinal substance is quickly absorbed from the administration site such as the oral mucous membrane into the body without hindering the movement of the ionic medicinal substance.

e. The medicinal substance can be fixed as needed on the surface or interior of dried polymer layer with water soluble and swelling properties or medicine layer so that administration rate by iontophoresis can be controlled by means of that fixed location.

f. The polymer layer with water soluble and swelling properties is dry so that it can contain a medicinal substance in large quantities and the efficiency of the administration is remarkably improved.

g. The polymer layer with water soluble and swelling properties is dry up until the time it is used so that the medicine which are quickly degrated by moisture can be used.

(2) Effectiveness of the Iontophoresis Device a. The ionotphoresis electrode has excellent safety and excellent property of administration of the medicinal substance so that medicine with polymer, physiologically active agents is efficiently absorbed into the blood circulation and the electrical stimulation (irritation) of the administration site or oral mucous membrane is extremely low.

b. The ionophoresis electrode is small and light-weight so it easily attaches even to narrow site of the oral mucous membranes, and by applying an electrical circuit outside the body, even a large dose of medicine can be easily administered.

c. The donor and reference device integrated with the ionotphoresis device have been made small so that attachment and administration of medicine even to narrow site of the oral mucous membrane is easy, and administration of the medicine is performed in an extreme efficient manner just as by making the attachment to the oral membrane.

TABLE 1

Stimulation Tests

| | |
|---|---|
| Embodiment 3 | None |
| Embodiment 4 | None |
| Embodiment 5 | None |
| Embodiment 6 | None |
| Comparison Example 1 | Present |
| Comparison Example 2 | Present |

TABLE 2

Stimulation Tests

| | |
|---|---|
| Embodiment 8 | No stimulation |
| Embodiment 9 | No stimulation |
| Comparison Example 1 | Stimulation present |

TABLE 3

Calcitonin Stimulation Tests

| | |
|---|---|
| Embodiment 13 | No stimulation |
| Embodiment 14 | No stimulation |
| Comparison Example 4 | Stimulation present |
| Comparison Example 5 | Stimulation present |

TABLE 4

Insulin Stimulation Tests

| | |
|---|---|
| Embodiment 15 | No stimulation |
| Embodiment 16 | No stimulation |
| Comparison Example 6 | Stimulation present |
| Comparison Example 7 | Stimulation present |

What is claimed is:

1. An iontophoresis unit for an oral mucous membrane for administering through an oral cavity into a living body an effective constituent to be ionized, the iontophoresis unit comprising:

an iontophoresis device comprising
  a) a backing layer;
  b) a conductive layer for current dispersion; and
  c) a spacer layer made of a dried polymer with water soluble and swelling properties, and containing the effective constituent;

a reference electrode; and a grasping device for grasping the mucosal membrane between the spacer layer and the reference electrode, the grasping device comprising an electric circuit electrically connecting said iontophoresis device and said reference electrode, and a power supply connected to said electric circuit.

2. A method for using iontophoresis for an oral mucous membrane for administering through an oral cavity into a living body an effective constituent to be ionized, the method comprising said iontophoresis unit according to claim 1, wherein said grasping device comprises two clamp-type grasping elements each having a contacting portion for contacting the oral mucous membrane;

said iontophoresis device is attached at the contacting portion of one of the clamp-type grasping devices for contacting the oral mucous membrane;

said reference electrode is attached at the contacting portion of the other of the clamp-type grasping elements; and said iontophoresis device is fixed to the oral mucous membrane by the grasping elements grasping the oral cavity when applied, the iontophoresis device having conductivity and sticking properties which are activated by mucous existing on the surface of the mucous membrane.

\* \* \* \* \*